United States Patent [19]

Lee

[11] 4,274,453
[45] Jun. 23, 1981

[54] ASEPTIC FLUID TRANSFER
[75] Inventor: Peter F. Lee, Edina, Minn.
[73] Assignee: Southland Instruments, Inc., Houston, Tex.
[21] Appl. No.: 13,078
[22] Filed: Feb. 21, 1979
[51] Int. Cl.³ .............................................. B65B 3/04
[52] U.S. Cl. ........................................ 141/1; 141/284; 141/329; 141/285; 141/392; 73/864; 73/24; 128/218 NV; 251/349; 356/39
[58] Field of Search .......... 141/329, 330, 19, 250-285, 141/129, 130, 1-12, 65, 66, 67, 83, 392; 73/42 R; 251/349, 354; 128/218 N, 218 NV; 356/39, 246

[56] References Cited
U.S. PATENT DOCUMENTS

| 578,944 | 3/1897 | Platz et al. | 141/329 |
| 2,193,059 | 3/1940 | Chapman | 141/329 |
| 2,415,419 | 2/1947 | Cozzoli | 141/329 |
| 3,383,923 | 5/1968 | Conche et al. | 73/421R |
| 4,041,994 | 8/1977 | Horwitz et al. | 141/329 |
| 4,170,798 | 10/1979 | Krumdieck | 73/421 R |

OTHER PUBLICATIONS

*Coulter Counter Model "S" SR* Coulter Electronics, 1964, Hialeah, Fla.

Primary Examiner—Houston S. Bell, Jr.
Attorney, Agent, or Firm—Merchant, Gould, Smith, Edell, Welter & Schmidt

[57] ABSTRACT

The combination of an automated hematology analyzer (21) with an input device (20) enabling closed transfer of blood to said analyzer to a sealed specimen container having a perforable closure, and the input device itself.

12 Claims, 9 Drawing Figures

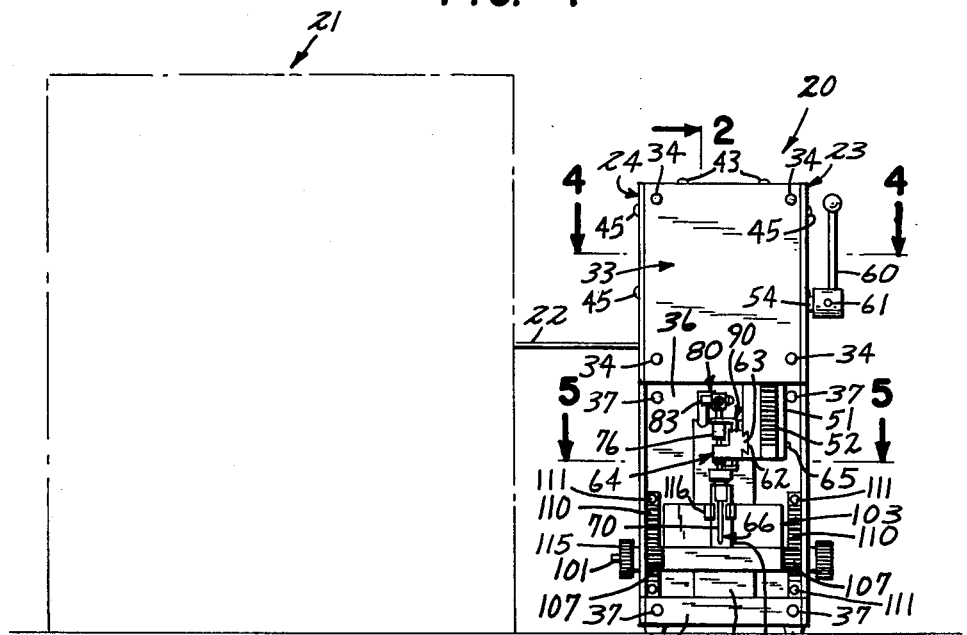
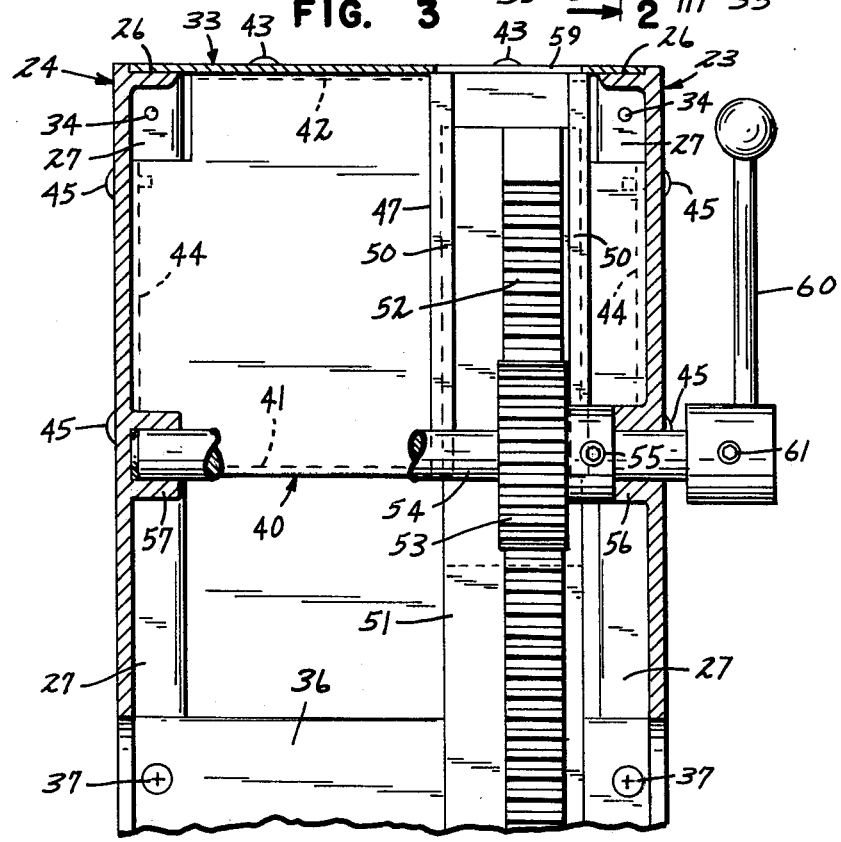

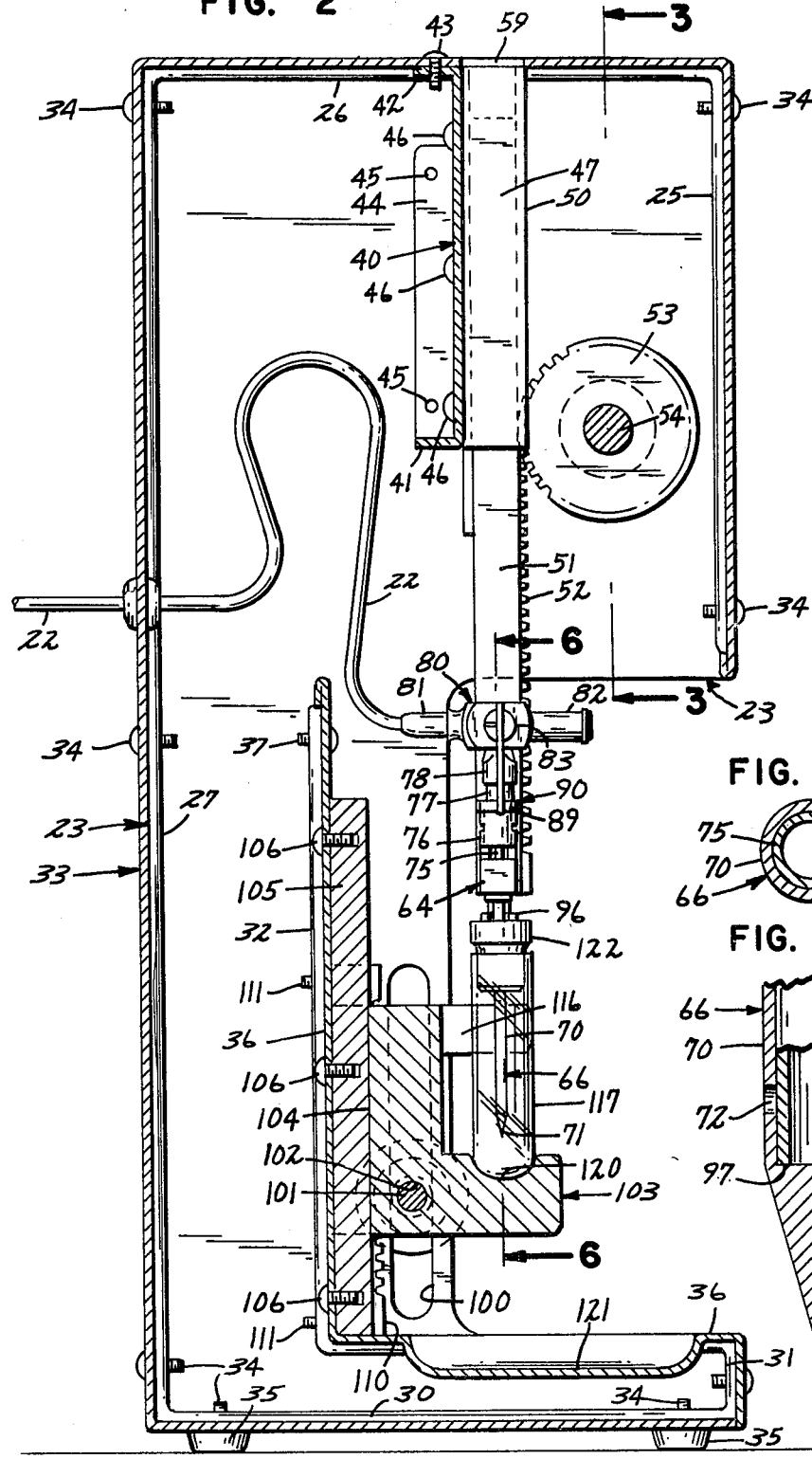

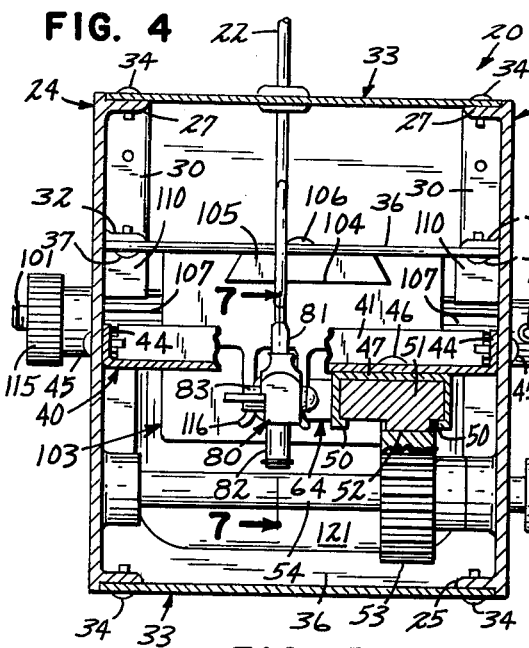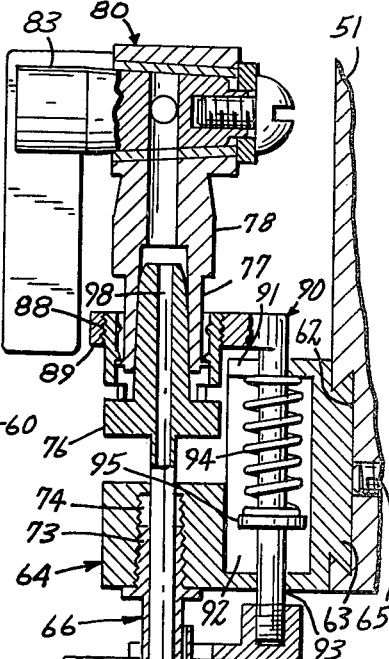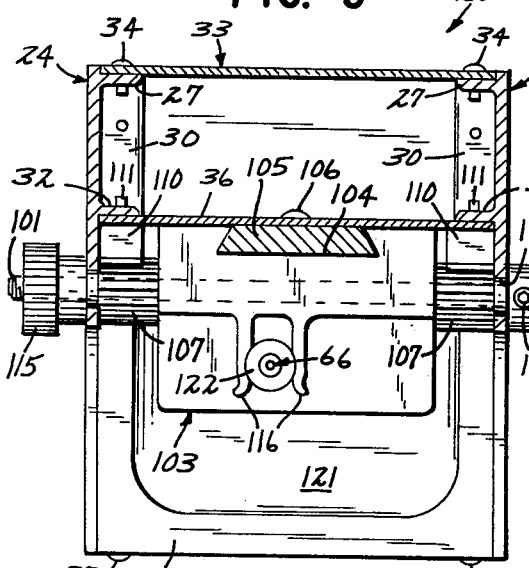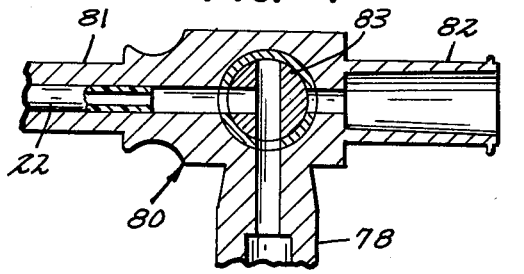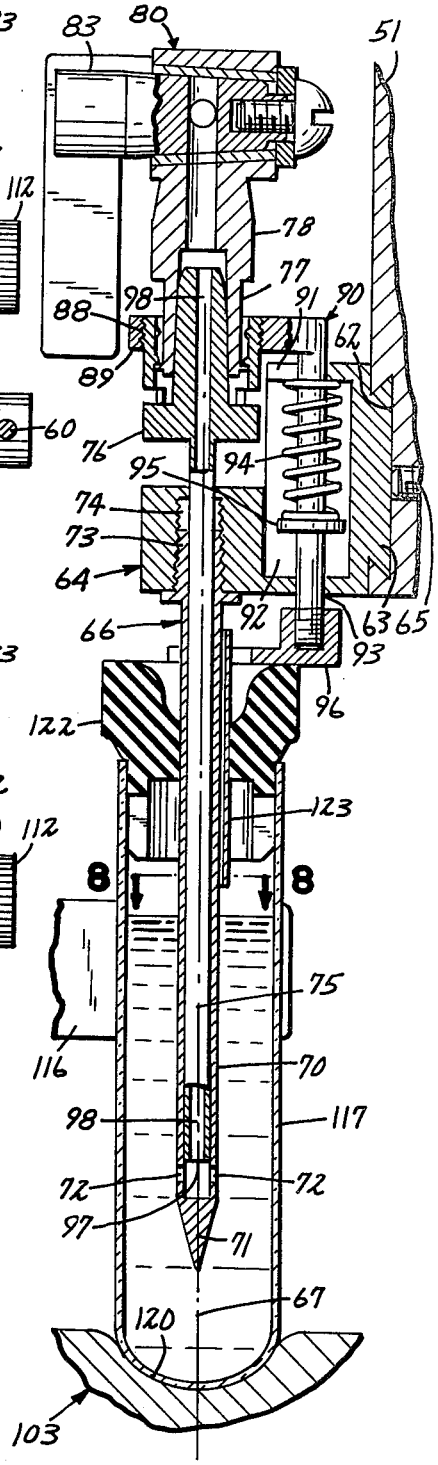

ASEPTIC FLUID TRANSFER

This invention relates to the field of medical technology, and specifically to apparatus and procedures for minimizing the occupational hazards of workers who perform routine blood testing using advanced technology.

BACKGROUND OF THE INVENTION

One the of the great advances in medical technology in recent years is the development of automated equipment for performing comprehensive analyses of blood samples to give readings of factors identified as red cell count, white cell count, hemoglobin, hematocrit, mean cell volume, mean cell hemoglobin and mean cell hemoglobin concentration. An automated hematology analyzer aspirates a specimen of blood from a sample container, performs the required tests, prints out the test results, and flushes the equipment in preparation for the next specimen, in a time interval less than one minute.

Samples of patient's blood are provided in 3½ ml sample containers having rubber stopper closures. Specimen input to the analyzer is both "open" and manual, that is, a technician must take a previously shaken sample container (or must shake the container a predetermined amount), open the container by removing the stopper, immerse the aspirator tip of the analyzer into the sample, and actuate the analyzer. After the specimen input has been completed, the container must be restoppered and disposed of, and any liquid adhering to the outside of the aspirator tip must be removed.

Because the sample container must be opened and manually introduced into the system, laboratory personnel is exposed to a potentially dangerous environment.

All laboratory specimens are regarded as hazardous. Pathogenic microorganisms are readily spread to laboratory personnel by direct contact. With blood samples there is particularly concern over exposure to serum hepatitis. The open input of blood specimens to automated systems as described above results in exposure of technicians to contact with the blood dripping from the aspirator tip on the equipment, as well as to residual blood in the container and on the rubber stopper.

SUMMARY OF THE INVENTION

My invention provides for a "closed" specimen input to the analyzer, by enabling transfer of blood from a closed container to the analyzer without exposing the technician to contact with the blood before or after aspiration. The unopened container is secured in a suitable holder: when a manual control is operated a compound transfer needle, connected by an aspiration tube to the analyzer, is forced to enter the container by penetrating the closure. The compound needle comprises an outer tubular member having a pointed tip and a side opening or cross bore, and an inner member sliding within the outer member to close or open the cross bore. During penetration the inner needle blocks the cross bore, preventing particles of the stopper from entering the system before or upon aspiration: as penetration is completed the inner member retracts to expose the cross bore and provide communication between the sample container and the analyzer. After aspiration of the sample, the compound needle is raised out of the container. The inner member simultaneously moves to again block the cross bore and so prevent drip of liquid, and both members are then withdrawn, the stopper material acting to wipe away liquid from the external surfaces of the members, and then to reseal the container. The result is an input method in which the technician is never exposed to contact with blood at any time.

Various advantages and features of novelty which characterize my invention are pointed out with particularity in the claims annexed hereto and forming a part hereof. However, for a better understanding of the invention, its advantages, and objects attained by its use, reference should be had to the drawing which forms a further part hereof, and to the accompanying descriptive matter, in which there is illustrated and described a preferred embodiment of the invention.

BRIEF DESCRIPTION OF THE DRAWING

In the drawing

FIG. 1 is an elevational view of the inventive structure associated with an automated hematology analyzer;

FIG. 2 is a view in section along the vertical line 2—2 of FIG. 1;

FIG. 3 is a fragmentary view in section along the vertical line 3—3 of FIG. 2,

FIG. 4 is a view in section along the horizontal line 4—4 of FIG. 1;

FIG. 5 is a view in section along the horizontal line 5—5 of FIG. 1;

FIG. 6 is a fragmentary view in section along the vertical line 6—6 of FIG. 2, to a larger scale;

FIG. 7 is a fragmentary view in section along the vertical line 7—7 of FIG. 4;

FIG. 8 is a fragmentary view in section along the line 8—8 of FIG. 6; and

FIG. 9 is a fragmentary showing of a portion of FIG. 6 in a second condition of the equipment.

DESCRIPTION OF THE PREFERRED EMBODIMENT

As is shown in FIG. 1 my invention comprises an input device 20 positioned adjacent a known automatic hematology analyzer 21 and connected thereto by an aspiration tube 22. Device 20 is assembled on a pair of end castings 23 and 24. Casting 23 is shown in FIG. 2 to have an upper front flange 25, a top flange 26, a rear flange 27, a bottom flange 30, a lower front flange 31, and a middle front flange 32. Casting 24 is similarly constructed.

Castings 23 and 24 are joined to a housing sheet 33 secured thereto by fasteners 34 which include feet 35, by a lower cross-panel 36 secured to flanges 32 and 31 by fasteners 37, and by an upper bracket 40 having a lower flange 41, an upper flange 42 secured to member 33 by fasteners 43, and side flanges 44 one of which is shown in FIG. 2 as secured to casting 23 by fasteners 45.

Secured to bracket 40 by fasteners 46 in a vertical channel 47 having inturned lips 50. (See FIG. 3) A slider 51 is free to move in channel 47 and is formed with a rack 52. A gear 53 meshing with rack 52 is secured on a shaft 54 by a fastener 55. Shaft 54 is carried in bearings 56 and 57 in castings 23 and 24 respectively, and projects beyond the former to carry a handle 60 secured in place by a fastener 61. Rotation of shaft 54 by operation of handle 60 acts through gear 53 and rack 52 to displace slider 51 vertically in channel 47. An opening 59 is provided in housing sheath 33 to permit upward protrusion of slider 51 if desired.

Slider 51 is longer than channel 47 and projects downwardly therefrom. Near its bottom a transverse dovetail groove 62 (See FIG. 6) is formed in slider 51, to receive the dovetailed tenon 63 of a saddle 64, the saddle accordingly being capable of sliding forward and rearward, and being locked in adjusted position by a suitable fastener 65.

Saddle 64 carries a compound needle 66 having an axis 67 aligned with the direction of movement of slider 51. Needle 66 comprises an outer tubular member 70 closed and pointed at one end 71, and provided with a cross bore 72 near that end. The other end of member 70 is provided with a threaded fitting 73 by which it may be secured in a tapped opening 74 in saddle 64. An inner tubular member 75 coaxial with member 70, within which it is a sliding fit, is provided at its upper end with a standard Luer fitting 76 for connection with a mating fitting 77 on the first branch 78 of a stopcock 80 having two further branches 81 and 82 and a valving plug 83. In the position of stopcock 80 shown in the drawings, communication is made between fitting 77 and aspirator tube 22, which passes through sheet 33 and is received in branch 81. Branch 82 may conveniently be in the form of a further Luer fitting to increase the versatility of the apparatus when the plug of stopcock 80 is rotated to alternative positions.

Fitting 76 is removably secured, as by a threaded connection 88, at one arm 89 of a mounting member 90 which passes through a slot 91 in saddle 64 and then through a vertical chamber 92 in the saddle, to pass out through an aperture 93 at the bottom of the saddle. Within chamber 92 a compression spring 94 surrounds member 90 and acts between saddle 64, above, and a shoulder 95 on member 90, below, to resiliently urge the mounting member downward, thus urging fitting 76 and inner member 75 downwardly with respect to outer member 70. Below saddle 64 mounting member 90 is connected to an actuator member 96, by which spring 94 may be compressed so that the tubular members are brought into the axial relation shown in FIG. 6, in which the lower end 97 of member 75 is above cross bore 72 and communication is established through the cross bore to a central bore 98 in member 75, and thence through fittings 76 and 77 and stopcock 80 to aspiration tube 22. If spring 94 is allowed to expand, member 75 moves downwardly until end 97 thereof occludes cross bore 72, and communication to aspiration tube 22 is interrupted.

Casting 23 is slotted at 100, (See FIG. 2) and casting 24 is similarly slotted. A shaft 101 extends through these slots, and turns in a bearing aperture 102 formed in a sample carrier 103 of generally L-shaped section in a vertical plane from front to rear. The rear surface of carrier 103 is formed as a dovetailed mortise 104, and a dovetailed tenon 105 is mounted on panel 36 by fasteners 106. Between the sides of carrier 103 and castings 23 and 24 a pair of gears 107 are secured to shaft 101 by suitable fasteners, (See FIG. 5) to mesh with a pair of vertical racks 110 secured to flanges 32 by fasteners 111. At one end of shaft 101 a knob 112 is secured thereto by a fastener 113. The other end of shaft 101 is externally threaded to receive an internally threaded knob 115. It will be evident that rotation of knob 112 rotates gears 107, thus acting through racks 110 to displace carrier 103 upwardly and downwardly along tenon 105, the position of the carrier then being lockable by rotation of knob 115 to grip the outer surface of casting 24.

A pair of resilient arms 116 extend forward from the top of carrier 103, and are spaced by slightly less than the diameter of a standard specimen container shown at 117. A cavity 120 is formed in carrier 103 to receive the rounded bottom of the container, and is located for alignment with axis 67 of compound needle 66. Panel 36 may be configured to provide a small storage tray 121 of this is desired.

The perforable closure or resilient stopper of container 117 is shown at 122 in FIG. 6, which also shows that the upper portion of outer member 70 carries or is configured to provide a conduit 123 extending generally parallel to axis 67.

OPERATION

In operation the aspiration tube 22 of analyzer 20 is passed through sheet 33 and inserted into branch 81 of stopcock 80, in which it makes a fairly good seal. The stopcock is turned to the position shown in FIG. 7. If necessary, fastener 65 is loosened and saddle 64 is moved forward or backward until axis 67 centers in cavity 120, and fastener 65 is secured. The connection between fittings 76 and 77 is made secure. Handle 60 is operated to raise compound needle 66 to a convenient height, spring 94 forcing inner member 75 downward to occlude cross bore 72. Knob 115 is loosened and carrier 103 is adjusted vertically until a container resting in cavity 120 and clamped between arms 116 has its closure 122 at a convenient small distance below point 71 of member 70.

The technician now shakes a sample container, or takes one from a shaking rack, sets its bottom in cavity 120, and presses it between arms 116 until the center of closure 122 is below the point 71 of needle 66, all without removing closure 122. Now by operation of handle 60 the needle is lowered until point 71 penetrates the closure and extends below the surface of blood in the container, conduit 123 slightly enlarging the penetration to provide a passage for ambient atmosphere into the upper part of the chamber. Note that at this time cross bore 72 is occluded, so that no particles of the closure can enter central bore 98.

As handle 60 is actuated, the needle nears the bottom of the container, when member 96 engages the top of closure 122, so that spring 94 is compressed and outer member 70 moves downward with respect to inner member 75 until cross bore 72 is uncovered, and communication with central bore 98 is accomplished. Conduit 123 is of such length that its lower end moves below the lower surface of closure 122 at about the same time that member 96 engages the upper surface of the closure, but does not reach the level of blood in a normally filled container. Operation of analyzer 21 may now be initiated in the usual fashion. This results in aspiration of a predetermined quantity of blood from container 117, and its replacement by an equal volume of air through conduit 123.

When specimen input is completed, handle 60 is operated in the opposite direction, to raise needle 66. The first increment of motion causes occlusion of cross bore by inner member 75, to prevent dripping of any residual blood from member 75. As handle 60 is further operated, needle 66 is withdrawn through closure 122, which not only reseals itself to prevent leakage of liquid therefrom, but also wipes off any residual liquid on the surface of the needles as it is withdrawn.

It is clear that by the structure described above the sampling of specimens of blood in standard containers is converted from an open process to a closed process, so that the technician is never in danger of contacting blood. The operation is not entirely automatic, but is no longer manual in the sense that a technician must open a container, position it below an aspiration tube, and raise it until the tube enters the liquid, nor must he now lower the container from around the aspirator tube, where there is a possibility of dripping of blood residual on the outer surface of the tube. It is also evident that the procedure of occluding cross bore 72 during passage of needle 66 through the closure in either direction prevents particles of closure material from being aspirated into the analyzer.

Numerous characteristics and advantages of my invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning of the terms in which the appended claims are expressed.

What is claimed is:

1. Aseptic liquid transfer apparatus comprising, in combination:
    a first tubular member extending along a vertical axis between a closed penetration end and an open end, and having a cross bore near said closed end;
    means mounting said first member for movement along said axis;
    a second tubular member having a central bore extending along an axis between first and second ends and having an outside diameter substantially the same as the inside diameter of said first member;
    means mounting said second member for limited axial relative movement within said first member between a first position, in which said first end of said second member occludes said cross bore, and a second position, in which said cross bore is in communication with said central bore;
    first actuating means for causing said movement of said first member;
    resilient means maintaining said second member in said first position during said movement of said first member; and
    second actuating means for causing movement of said second member from said first position to said second position in opposition to said resilient means.

2. Apparatus according to claim 1 and means for applying suction to said second end of said second member.

3. Apparatus according to claim 1 further including means for mounting a container having a resilient penetrable upper closure in axial alignment with said penetration end of said first tubular member, so that said first actuating means may cause said members to penetrate said closure and enter said container, and so that said second actuating means may subsequently engage said closure to cause movement of said second member into said second position; and
    means for applying suction to said second end of said second member to draw liquid from said container through said cross bore and said central bore.

4. Apparatus according to claim 3 and means carried by said first member for admitting ambient air to said container to replace liquid drawn therefrom.

5. In combination, a manually operable automated hemotology analyzer and an input device connected thereto for enabling closed transfer of a specimen of blood to said analyzer from a sealed sample container having a resilient, penetrable closure.

6. The combination of claim 5 in which said device comprises a compound needle having a central bore extending along a longitudinal axis thereof, a terminal cross bore, and means for establishing and terminating communication between said bore and said cross bore, a sample container holder, and means operable to cause said needle to penetrate the closure of a container in said holder to, establish said communication, to terminate said comunication, and to withdraw through said closure.

7. The combination of claim 6 in which the last named means includes a slider, means mounting said slider for vertical movement, means for reversibly causing said vertical movement of said slider, and means mounting said compound needle on said slider, including means enabling limited movement of said needle transverse to said axis.

8. The combination of claim 6 in which said holder includes adjusting means enabling movement thereof in the direction of said axis of said needle, and means for locking said adjusting means.

9. The combination of claim 6 in which needle includes means for admitting replacement air to said container while said communication is established.

10. The aseptic method of transferring blood from a container sealed by a resilient penetrable closure which comprises the steps of:
    positioning the container with the closure uppermost;
    penetrating said closure by a tubular member having a closed cross bore at its lower end, the size of said tubular member and the resilience of said closure being such that the penetration made thereby in said closure is self-sealing upon withdrawal of said member;
    unclosing the cross bore; and
    aspirating blood from said container through said cross bore and said tubular member while admitting replacement air to said container through said penetration.

11. The method according to claim 10 which comprises the further steps of:
    closing said cross bore to prevent dripping of residual blood from said member therethrough, and
    withdrawing said tubular member upward through said closure so that the latter wipes residual blood from the surface of said member and reseals said container.

12. The method of obtaining a blood specimen for an automatic hemotology analyzer which comprises the steps of connecting the analyzer to a tubular member having a closed cross bore;
    positioning a container of blood, sealed by a resilient penetrable closure, with the closure uppermost;
    penetrating the closure by said tubular member;
    unclosing the cross bore;
    and aspirating blood from said container through said cross bore and tubular member while admitting replacement air to said container through the penetration.

* * * * *